(12) United States Patent
Hur et al.

(10) Patent No.: US 9,599,542 B2
(45) Date of Patent: Mar. 21, 2017

(54) SAMPLE ANALYZING CHIP

(71) Applicant: NANOENTEK, INC., Seoul (KR)

(72) Inventors: Dae Sung Hur, Suwon-si (KR); Jae Jeong Kim, Hwaseong-si (KR); Yu Rae Kim, Hwaseong-si (KR)

(73) Assignee: NANOENTEK, INC., Seoul (KR)

( * ) Notice: Subject to any disclaimer, the term of this patent is extended or adjusted under 35 U.S.C. 154(b) by 382 days.

(21) Appl. No.: 14/401,140

(22) PCT Filed: May 14, 2013

(86) PCT No.: PCT/KR2013/004263
§ 371 (c)(1),
(2) Date: Nov. 14, 2014

(87) PCT Pub. No.: WO2013/172631
PCT Pub. Date: Nov. 21, 2013

(65) Prior Publication Data
US 2015/0101422 A1   Apr. 16, 2015

(30) Foreign Application Priority Data

May 14, 2012 (KR) .................. 10-2012-0050704

(51) Int. Cl.
*G01N 35/08* (2006.01)
*G01N 1/00* (2006.01)
(Continued)

(52) U.S. Cl.
CPC .......... *G01N 1/00* (2013.01); *B01L 3/502715* (2013.01); *B01L 3/502723* (2013.01);
(Continued)

(58) Field of Classification Search
CPC ....... B01L 2200/027; B01L 2200/0684; B01L 2300/0816; B01L 2300/089;
(Continued)

(56) References Cited

U.S. PATENT DOCUMENTS 6,156,270 A     12/2000  Buechler
2004/0125266 A1  7/2004  Miyauchi et al.
(Continued)

FOREIGN PATENT DOCUMENTS

EP     0674009 A2    9/1995
JP     2007-163459 A 6/2007
(Continued)

OTHER PUBLICATIONS

International Search Report for PCT/KR2013/004263 mailed Aug. 30, 2013 from Korean Intellectual Property Office.

*Primary Examiner* — Jennifer Wecker
(74) *Attorney, Agent, or Firm* — Paratus Law Group, PLLC

(57) ABSTRACT

The present invention relates to a sample analyzing chip. The chip can prevent upper and lower substrates of a channel from being attached to each other due to deflection on a micro channel and can solve the problem of the sample drying up within a measuring time of a target. Also, the chip can prevent bubbles from being generated in a central portion of the micro channel.

12 Claims, 24 Drawing Sheets

(51) Int. Cl.
 *G01N 33/48* (2006.01)
 *B01L 3/00* (2006.01)

(52) U.S. Cl.
 CPC ........ *B01L 3/502746* (2013.01); *G01N 33/48* (2013.01); *B01L 2200/027* (2013.01); *B01L 2200/0684* (2013.01); *B01L 2300/089* (2013.01); *B01L 2300/0816* (2013.01); *B01L 2400/086* (2013.01); *G01N 35/08* (2013.01); *G01N 2001/002* (2013.01)

(58) Field of Classification Search
 CPC ......... B01L 2400/086; B01L 3/502715; B01L 3/502723; B01L 3/502746; G01N 1/00; G01N 2001/002; G01N 33/48
 See application file for complete search history.

(56) References Cited

U.S. PATENT DOCUMENTS

| | | |
|---|---|---|
| 2005/0229696 A1* | 10/2005 | Takayama ............. B01F 5/0646 73/204.26 |
| 2007/0116594 A1 | 5/2007 | Shimizu et al. |
| 2007/0269893 A1 | 11/2007 | Blankenstein et al. |
| 2007/0298433 A1 | 12/2007 | Sia et al. |
| 2010/0261205 A1 | 10/2010 | Kakuta et al. |
| 2011/0243795 A1* | 10/2011 | Park .................. B01L 3/502746 422/68.1 |

FOREIGN PATENT DOCUMENTS

| | | |
|---|---|---|
| JP | 2007-187616 A | 7/2007 |
| KR | 10-2004-0038806 A | 5/2004 |
| KR | 10-2008-0084844 A | 9/2008 |

* cited by examiner

Fig. 16
50
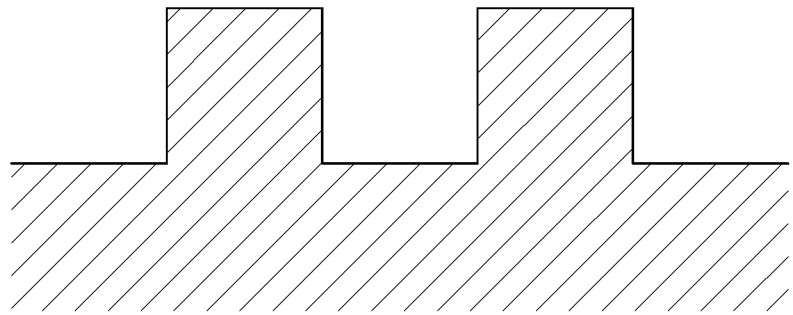
(a)
50
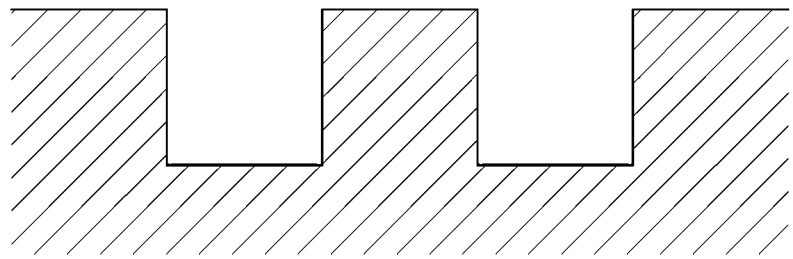
(b)

SAMPLE ANALYZING CHIP

CROSS REFERENCE TO PRIOR APPLICATIONS

This application is a National Stage Patent Application of PCT International Patent Application No. PCT/KR2013/004263 (filed on May 14, 2013) under 35 U.S.C. §371, which claims priority to Korean Patent Application No. 10-2012-0050704 (filed on May 14, 2012), which are all hereby incorporated by reference in their entirety.

TECHNICAL FIELD

The present invention relates to a sample analyzing chip, and more particularly, a sample analyzing chip capable of preventing an injected sample from drying during measurement and stabilizing flow of the sample as soon as possible to stably perform sample measurement and analysis even when the amount of the injected sample is very small.

BACKGROUND ART

In general, a fluid sample analysis has been extensively used in various fields including the field of chemical and biotechnology, the field of diagnosis using an analysis of blood or body fluids collected from a patient, etc. Recently, various compact analysis and diagnosis apparatuses and various analysis and diagnosis techniques have been developed to perform the fluid sample analysis in an easier and more efficient manner.

An analysis chip which is one of the analysis and diagnosis apparatuses has been frequently used to observe targets contained in an injected sample and count the number of the targets or measure the mobility of the targets.

Among such analysis chips, there is a growing need for a diagnosis chip for measuring the number or mobility of sperm. This is because the number of infertile couples have recently increased all over the world due to an increase in the number of endocrine disrupters caused by industrialization, unusual weather and environmental pollution caused by global warming, a change in social environment and lifestyle such as high nutrition or stress, etc., and male infertility which is one of various causes of infertility has recently increased.

When the existing tests are used to measure the number and mobility of sperm, expensive equipment and a lot of time and manpower are required. Thus, there is a growing need for an analysis chip enabling a test to be performed exactly in an easy manner.

When a disease is diagnosed, the number and functions of representative blood cells included in blood, e.g., red blood cells, white blood cells, platelets, etc., are inspected. In general, tuberculosis, obesity, pregnancy, etc. are tested based on a sedimentation speed of red blood cells, and dehydration, anemia, etc. are tested based on the volume of blood cells.

Chronic leukemia may be tested based on the number of platelets. Nephritis, hypoxia, smoking, a pulmonary disease, hemolytic anemia, aplastic anemia, etc. may be tested based on the number of red blood cells. Acute appendicitis, leukemia, aplastic anemia, etc. may be tested based on the number of white blood cells. Accordingly, measurement of the number of cells such as blood cells is closely related to a disease diagnosis.

In addition, there is a growing need for a sample analyzing chip in the field of food or the field of biotechnology to observe bacteria, yeast, mold, etc. Many experiments and research have been conducted in relation to the sample analyzing chip.

However, in the sample analyzing chip, a sample is caused to flow in a channel with a micro-height and a target is observed on a target location. The lower height of the channel, the more the channel may sag. Accordingly, the upper and lower substrates of the channel may be adhered to each other.

Also, in most cases, a very small amount of sample is used. Thus, the sample is likely to dry and cannot thus be measured before a target is measured after the sample is injected and the flow of the sample is sufficiently stabilized.

Also, when a sample rapidly flows along a wall surface of a micro channel, the sample is not likely to flow stably and bubbles may occur at a midpoint on the micro channel.

Accordingly, in order to solve these problems, there is a growing need for a sample analyzing chip capable of preventing a sample from drying while measurement is performed, and stabilizing the flow of the sample as soon as possible, thereby performing sample measurement and analysis in an easy and convenient manner.

DISCLOSURE OF THE INVENTION

Technical Problem

One or more embodiments of the present invention are to prevent upper and lower substrates of a channel to being adhered to each other due to deflection on a micro channel.

One or more embodiments of the present invention are to solve the problem of the sample drying up within a measuring time of a target when a very small amount of sample is injected.

One or more embodiments of the present invention are to prevent bubbles from being generated due to different between flow rate of a sample caused by a wall surface of a micro channel.

One or more embodiments of the present invention are to minimize a time required to stabilize the flow of a sample, thereby reducing a time required to measure micro cells.

Technical Solution

In accordance with the present invention, the above and other objects can be accomplished by the provision of a sample analyzing chip comprising: a micro channel formed between a upper substrate and a lower substrate to each other, and including a micro pillar and a bubble prevention channel; an inlet formed at one side of the micro channel, and including a first bottleneck configured to control a flow and flow rate of an injected sample and delay drying of the sample; and, an outlet formed at another side of the micro channel, and including a second bottleneck configured to delay flowing of the sample out from the micro channel and drying of the sample.

The micro pillar is formed on at least one of the upper substrate and lower substrate to maintain a height of the micro channel.

The bubble prevention channel is formed by a step formed in a peripheral region near the micro channel, and configured to suppress bubbles by minimizing the difference between flow rate of the sample when the sample flows.

The sample analyzing chip in accordance with the present invention, further comprises a grid formed to observe the sample on the micro channel.

The inlet comprises: a drop hole formed in the upper substrate and through which the sample is injected into the sample analyzing chip; and, a curved surface portion forming an inclined curved surface toward the drop hole.

The inlet further comprises an inlet chamber forming a space between the upper substrate and lower substrate, and configured to accommodate the sample injected via the drop hole.

The inlet further comprises an opening formed at a side of the drop hole and configured to cause the injected sample to smoothly flowing toward the micro channel without forming an interface.

The grid is formed in an embossed or engraved shape according to the type of the injected sample.

The upper substrate and the lower substrate are combined by bonding a bonding area to each other, wherein the bonding area protrude from edges of a bottom surface of the upper substrate and a top surface of the lower substrate around the micro channel.

The outlet comprises: an open hole formed at a side of the outlet opposite to the micro channel; and, an outlet chamber forming a space between the upper substrate and lower substrate, and configured to accommodate the sample flowing out from the micro channel so as to stabilize the overall flow of the sample.

In accordance with the present invention, the above and other objects can be accomplished by the provision of a sample analyzing chip comprising: a micro channel; at least one micro pillar formed to maintain a height of the micro channel; a grid formed to observe a sample on the micro channel; and, a bubble prevention channel configured to suppress bubbles from being generated when the sample flows near the micro channel.

In accordance with the present invention, the above and other objects can be accomplished by the provision of a sample analyzing chip comprising: an inlet into which a sample is injected; a micro channel communicating with the inlet to cause the injected sample to flow, an outlet through which the sample flows out from the micro channel; and, a bottleneck formed between the inlet and the micro channel and between the outlet and the micro channel to provide a narrower path than the micro channel, wherein the micro channel comprises: a micro pillar configured to maintain a height of a section in which the sample flows; and, a grid formed to observe the sample.

Advantageous Effects

According to one or more embodiments of the present invention, the upper and lower substrates of the channel may be prevented from being adhered to each other due to deflection on a micro channel.

Also, when a very small amount of sample is injected, the present invention may solve the problem of the sample drying up within a measuring time of a target.

Also, bubbles may be prevented from being generated due to different between flow rate of a sample caused by a wall surface of a micro channel.

Also, a time required to stabilize the flow of a sample may be minimized to reduce a time required to measure micro cells.

DESCRIPTION OF THE DRAWINGS

FIG. 16 is a partial cross-sectional view of an embossed or engraved grid of a sample analyzing chip according to an embodiment of the present invention.

MODE OF THE INVENTION

Figure 1:
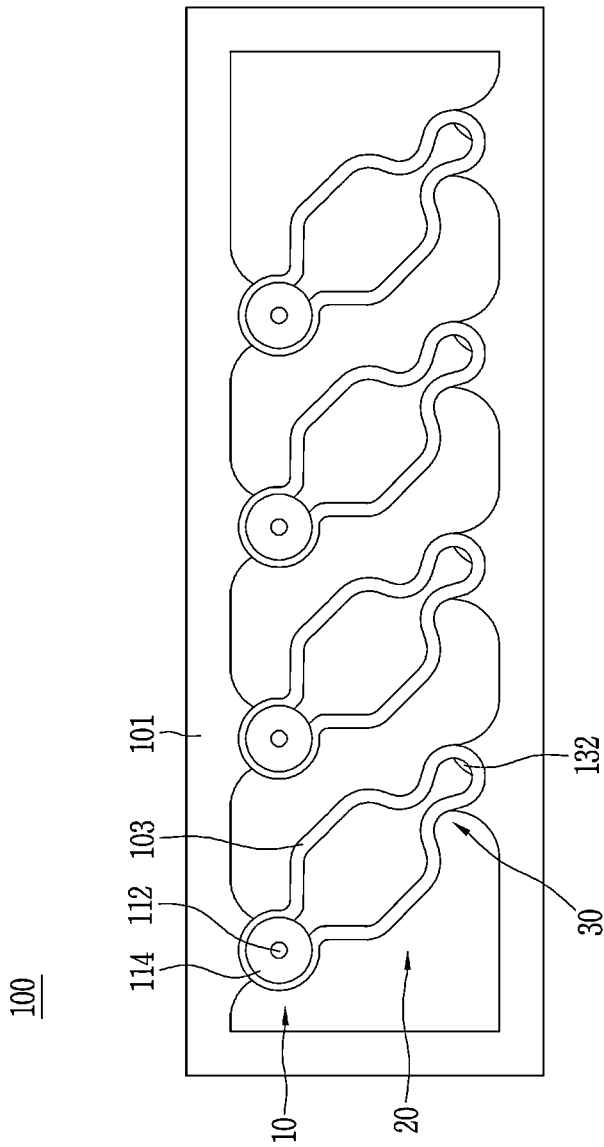
FIG. 1 is a plan view of a upper substrate of a sample analyzing chip according to an embodiment of the present invention.

Hereinafter, exemplary embodiments of the present invention will be described in detail with reference to the accompanying drawings. However, the present is not limited to these embodiments and may be embodied in many different forms. Rather, these embodiments are provided so that this disclosure will be thorough and complete, and will fully convey the scope of the invention to those skilled in the art. In the drawings, the same reference numerals denote the same elements.

Figure 2:
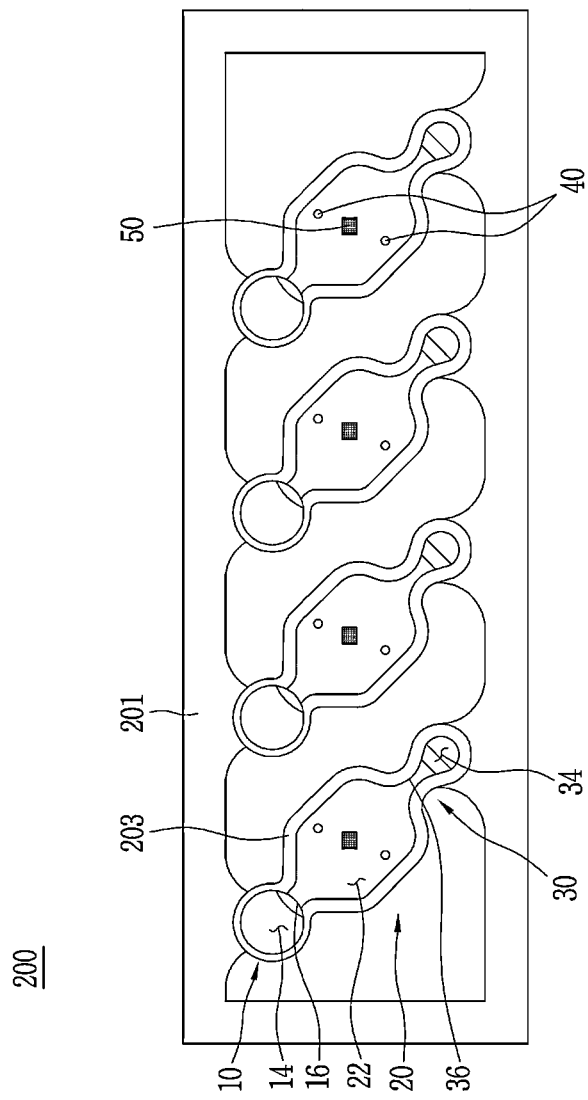
FIG. 2 is a plan view of a lower substrate of a sample analyzing chip according to an embodiment of the present invention.
Figure 3:
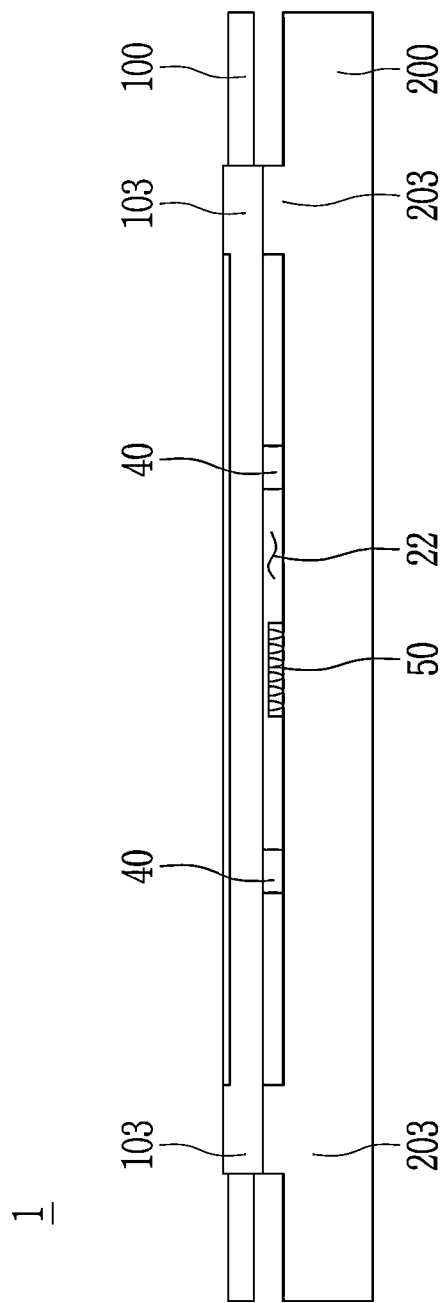
FIG. 3 is a cross-sectional view of a micro pillar and a grid structure of a sample analyzing chip according to an embodiment of the present invention.
Figure 4:
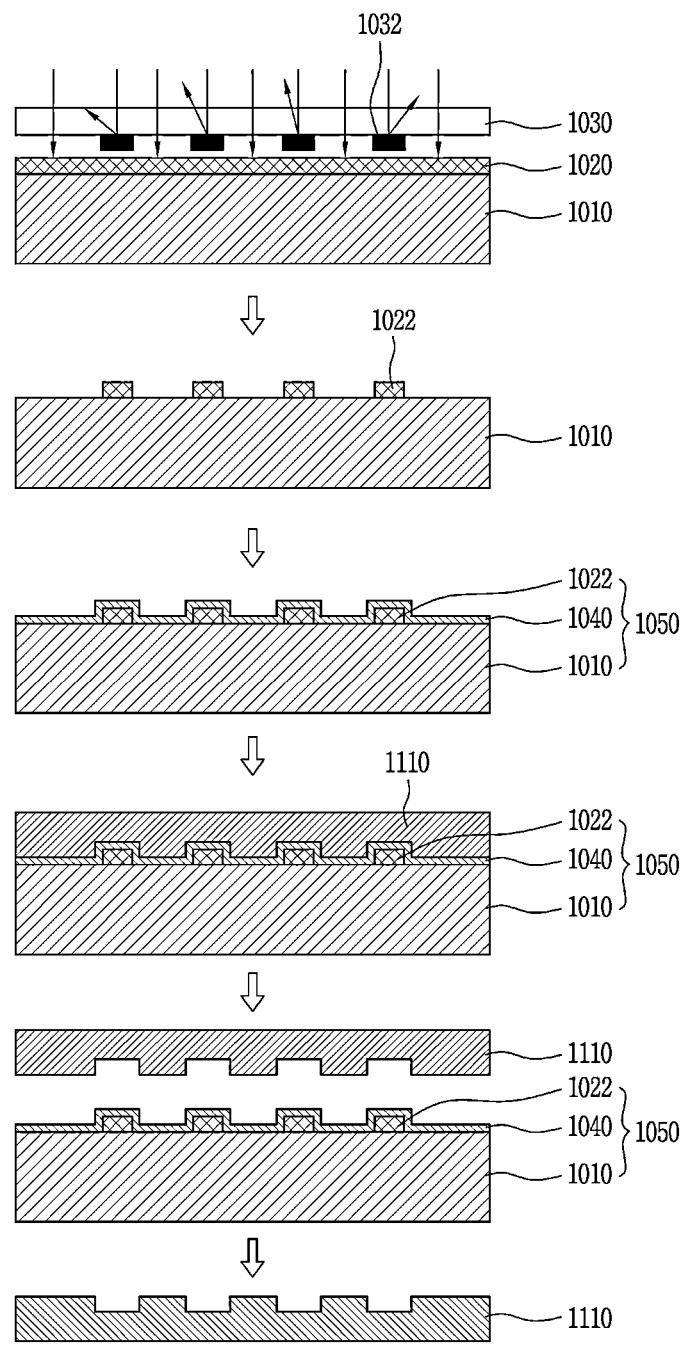
FIG. 4 is a process chart of a process of manufacturing a stamper for forming a sample analyzing chip according to an embodiment of the present invention.

FIG. 1 is a plan view of an upper substrate of a sample analyzing chip according to an embodiment of the present invention. FIG. 2 is a plan view of a lower substrate of a sample analyzing chip according to an embodiment of the present invention. FIG. 3 is a cross-sectional view of a micro pillar and a grid structure of a sample analyzing chip according to an embodiment of the present invention. FIG. 4 is a process chart of a process of manufacturing a stamper for forming a sample analyzing chip according to an embodiment of the present invention.

Referring to FIGS. 1 to 4, a sample analyzing chip 1 according to an embodiment of the present invention may largely include a micro channel 22 formed between a upper substrate 100 and a lower substrate 200 adhered to each other, at least one micro pillar 40 formed on at least one of the upper substrate 100 or the lower substrate 200 to maintain a height of the micro channel 22, and a grid 50 formed on the micro channel 22 to observe a sample.

The sample analyzing chip 1 may be disassembled into the upper substrate 100 and the lower substrate 200, and the upper substrate 100 and the lower substrate 200 are combined to form a body. According to an embodiment of the present invention, the sample analyzing chip 1 may be manufactured such that four sample analyzing chips 1 form a set to reduce costs per each test.

That is, upper structures of four sample analyzing chips 1 are integrally formed on an upper substrate frame 101 in the upper substrate 100 as illustrated in FIG. 1, and lower structures of the four sample analyzing chips 1 are integrally formed on a lower substrate frame 201 in the lower substrate 200 as illustrated in FIG. 2.

Then, the upper substrate 100 and the lower substrate 200 are combined to form a set of the four sample analyzing chips 1. Each of the four sample analyzing chips 1 may be largely divided into an inlet 10, a body portion 20, an outlet 30, etc.

In the present embodiment, the upper substrate 100 may include only macro structures that are relatively large, and be manufactured by plastic injection molding using a mold. In this case, the upper substrate may be formed in even a micro pattern of 100 μm by transferring the micro pattern onto a thin film.

The lower substrate 200 may include a micro-scale or nano-scale micro pattern, such as the at least one micro pillar 40 or the grid 50. In this case, the lower substrate 200 may be manufactured by injection molding after a stamper 1110 is manufactured using a micro electro mechanical systems (MEMS) process.

The stamper 1110 is manufactured to form a micro pattern for forming nano and/or micro-level micro channel and a form such as a grid or a pillar.

The stamper 1110 is manufactured using a micro electro mechanical systems (MEMS) technique or a nano electro mechanical systems (NEMS) technique. Referring to FIG. 4, in order to manufacture the stamper 1110, a photoresist (PR) 1020 which is a photosensitizer is applied onto a substrate 1010 using equipment such as a spin coater, a spray coater, or a dry-film laminator.

Here, the substrate 1010 may be a glass substrate or a silicon substrate formed to a thickness of 0.5 mm to 10 mm by mirror polishing. The photoresist 1020 may be a photosensitive material, and the thicknesses of a micro pattern and a channel to be formed on the stamper 1110 may be controlled by adjusting the thickness of the photoresist 1020.

After the photoresist 1020 is applied, the substrate 1010 on which the photoresist 1020 is applied may be soft-baked. In this case, the photoresist 1020 may be baked at 70° C. to 120° C. for one minute to thirty minutes.

After coating process of the photoresist 1020 is completed, a mask 1030 in which micro forms 1032 to be formed in a chip are patterned is disposed on the photoresist 1020. Here, a film mask or a chrome mask may be used according to the precision of a micro pattern to be formed in a chip. The chrome mask may be used since a micro pattern may be formed therein with a precision of about 1 μm.

After alignment of the mask 1030 is completed, exposure is performed by photolithography. Light emitted from a light source during a photolithographic process is converted into a collimated beam through a collimating optical system (not shown) and the collimated beam is incident on the mask 1030. The collimated beam incidented on the mask 1030 is projected according to the pattern of the micro forms 1032 patterned in the mask 1030 and is then incident on the photoresist 1020.

After the photolithography process is completed, an additional developing process is performed to leave or remove the photoresist 1020 that does not react with the collimated beam. The developing process may be performed using a dipping method to dip the photoresist 1020 into a room-temperature developing solution. Post-baking is performed to sufficiently harden the residual photoresist 1022.

Through the photolithography process, a plurality of photoresists 1020 may be stacked in a desired form to form a multilayer photoresist layer.

Through the developing process, the residual photoresist 1022 on the substrate 1010 becomes a round frame of the stamper 1110. The location, shape, and size of the round frame may vary according to the shape or size of a chip to be manufactured using the stamper 1110.

After the micro pattern is formed, a metal thin film 1040 is coated onto the substrate 1010 and residual photoresist 1022. In general, the metal thin film 1040 is coated using a metal such as chromium (Cr), silver (Ag), copper (Cu), nickel (Ni), gold (Au), etc. Thus, the substrate 1010, the residual photoresist 1022, and the metal thin film 1040 form a master 1050 for manufacturing the stamper 1110.

After the metal thin film 1040 is coated, the substrate 1010 is mounted into plating equipment and nickel electroplating is performed on the substrate 1010. Alternatively, the substrate 1010 may be plated with another material other than nickel. In this case, an electric current of several amperes is supplied in each step. A nickel-plated area of the substrate 1010 is the stamper 1110.

When the stamper 1110 is plated by nickel electroplating, the master 1050 and the stamper 1110 are separated from each other. When the thickness and flatness of the stamper 1110 are not equal to desired levels, chemical mechanical planarization (CMP) is performed to adjust the thickness of the stamper 1110 to be equal to the desire thickness. When the stamper 1110 is cut according to a mold by dicing, the manufacture of the stamper 1110 is completed. In this case, a pattern to be formed in a chip is transferred onto a surface of the separated stamper 1110 in an engraved shape.

Examples of the stamper 1110 may include an embossed stamper and an engraved stamper. Although the stamper 1110 manufactured in the above process is an engraved stamper, an embossed stamper may be manufactured using the engraved stamper 1110 and the master 1050 may be manufactured to match the embossed stamper.

The stamper 1110 manufactured in the above process is installed on an inner wall of a mold (not shown) and a closed space formed in the mold forms a whole shape of a chip. A chip corresponding to the closed space is manufactured by injecting resin into the closed space.

Although a case in which a macro-pattern is formed on the upper substrate 100 by plastic injection molding using a general mold and a micro pattern is formed on the lower substrate 200 using the stamper 1110 has been described above in the present embodiment, the reverse is possible and both the upper substrate 100 and the lower substrate 200 may be manufactured using the stamper 1110.

The upper substrate 100 and the lower substrate 200 may be combined with each other by bonding an upper-substrate bonding area 103 and a lower-substrate bonding area 203 which protrude from around edges of a bottom surface of the upper substrate 100 and a top surface of the lower substrate 200. In detail, the upper substrate 100 and the lower substrate 200 may be bonded to each other using solvent bonding method by applying an adhesive solvent on the upper substrate frame 101 and the lower substrate frame 201 and the upper-substrate bonding area 103 and the lower-substrate bonding area 203.

However, embodiments of the present invention are not limited thereto and the upper substrate 100 and the lower substrate 200 may be combined with each other using various bonding methods using heat bonding, plasma, pressure, ultrasonic waves, an organic solvent, etc.

The sample analyzing chip 1 may be used to inspect the number or mobility of sperm, platelets, blood cells, bacteria, yeast, mold, etc. To observe such a micro target, the micro channel 22 formed between the upper substrate 100 and the lower substrate 200 may have a height of several μm to several tens of μm, and preferably, about 10 μm to 20 μm.

As described above, since the height of the micro channel 22, i.e., the distance between upper substrate 100 and the lower substrate 200 forming a channel, is very small, the micro channel 22 may sag at a midpoint thereof. Accordingly, the upper substrate 100 and the lower substrate 200 may be adhered to each other.

According to an embodiment of the present invention, the sample analyzing chip 1 may include at least one micro pillar 40 to prevent the sample analyzing chip 1 from sagging and maintain the height of the micro channel 22. Here, at least one micro pillar 40 may be formed at an appropriate point on the body portion 20 in which the micro channel 22 is formed so as to prevent the upper substrate 100 from sagging.

Although in the present embodiment, two micro pillars 40 are formed to be symmetrical to both sides of the grid 50 of the lower substrate 200 so as to support the upper substrate 100 as illustrated in FIG. 3, the at least one micro pillar 40 may be formed on the upper substrate 100. In any case, the at least one micro pillar 40 is formed at the same height as the micro channel 22 to maintain the height of the micro channel 22.

The number, height, location, etc. of the at least one micro pillar 40 may vary according to the size and shape of the sample analyzing chip 1, the type of a sample, etc.

Figure 5:
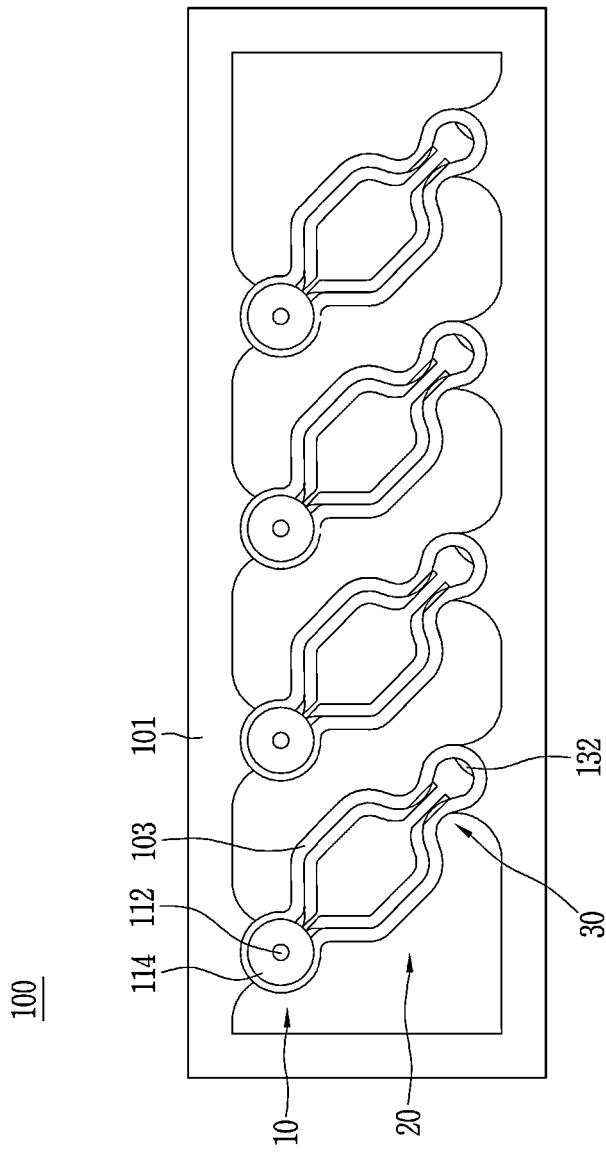
FIG. 5 is a plan view of an upper substrate of a sample analyzing chip to which a bubble prevention channel is applied according to an embodiment of the present invention.
Figure 6:
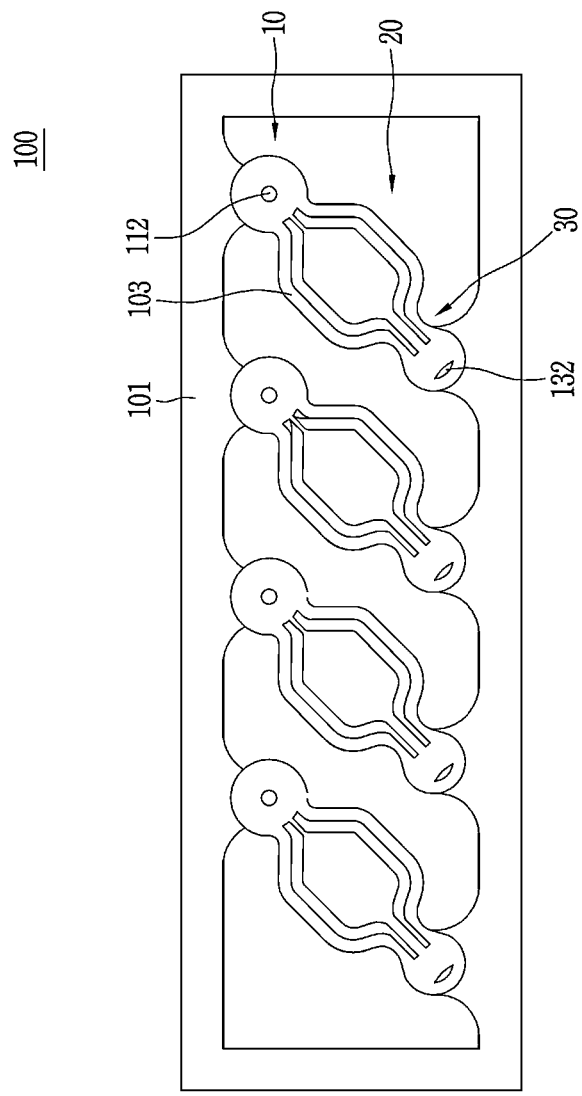
FIG. 6 is a bottom view of an upper substrate of a sample analyzing chip to which a bubble prevention channel is applied according to an embodiment of the present invention.
Figure 7:
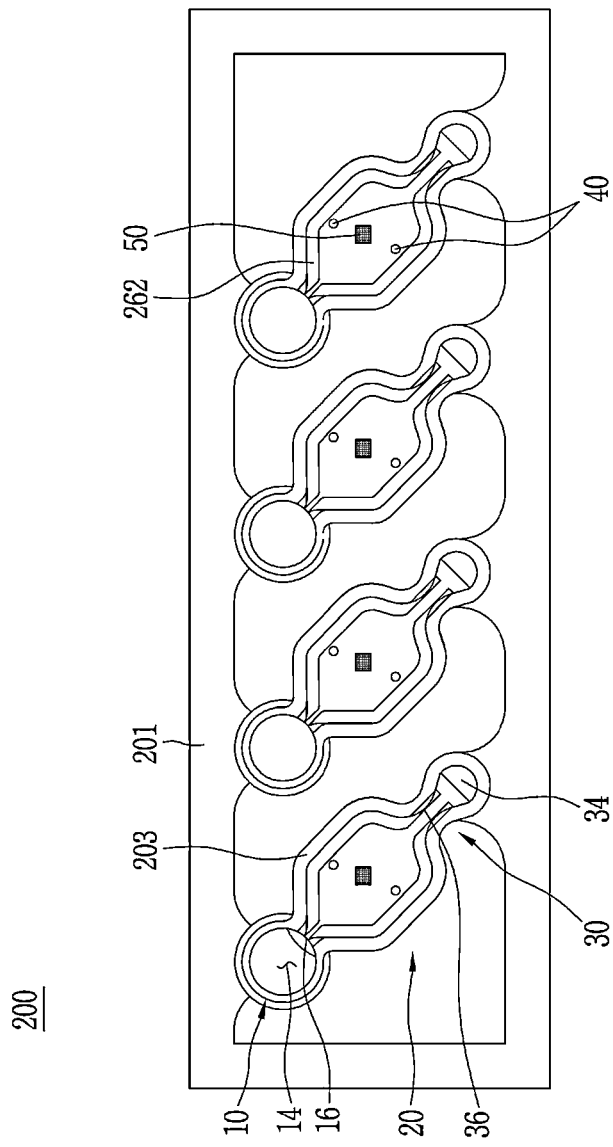
FIG. 7 is a plan view of a lower substrate of a sample analyzing chip to which a bubble prevention channel is applied according to an embodiment of the present invention.
Figure 8:
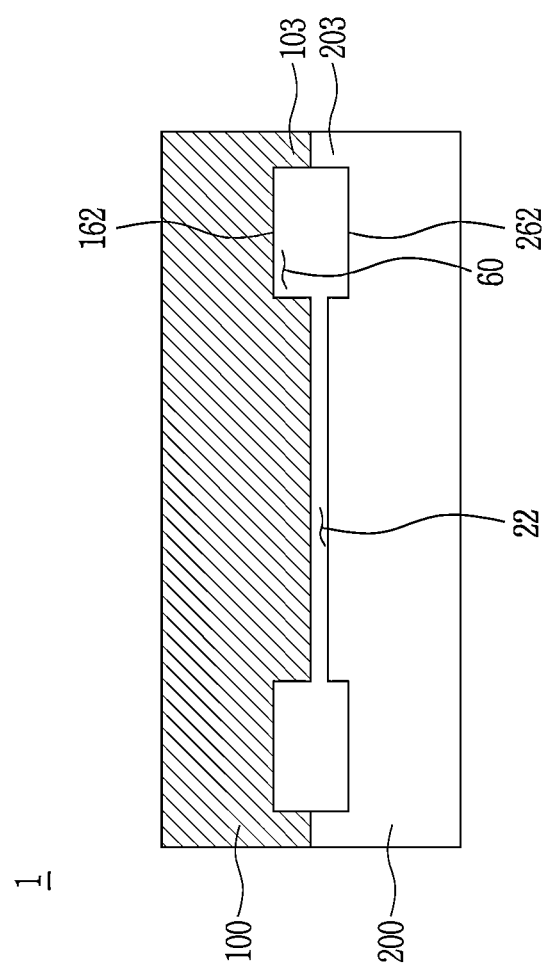
FIG. 8 is a cross-sectional view of a sample analyzing chip to which a bubble prevention channel is applied according to an embodiment of the present invention.
Figure 9:
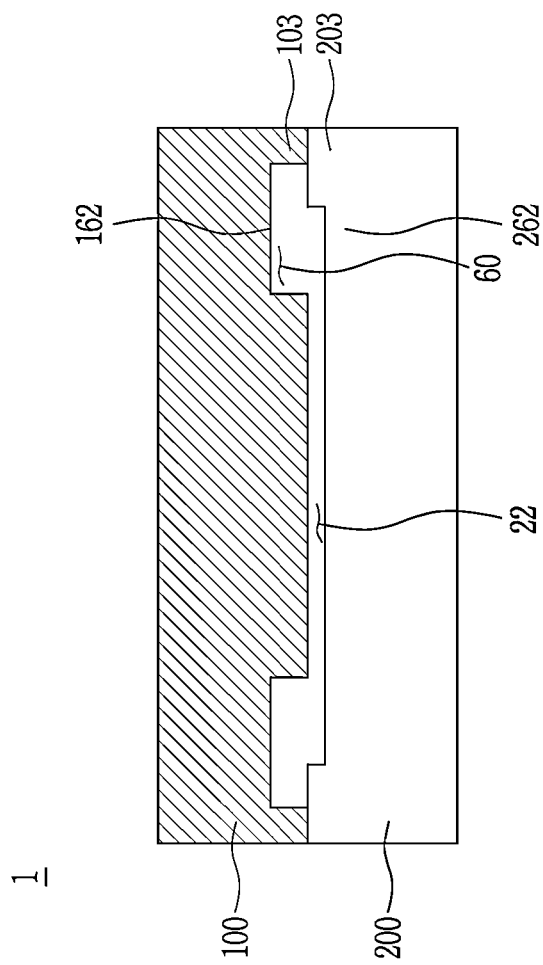
FIG. 9 is a cross-sectional view of a sample analyzing chip to which a bubble prevention channel of another form is applied according to an embodiment of the present invention.

FIG. 5 is a plan view of a upper substrate of a sample analyzing chip to which a bubble prevention channel is applied according to an embodiment of the present invention. FIG. 6 is a bottom view of upper substrate of a sample analyzing chip to which a bubble prevention channel is applied according to an embodiment of the present invention. FIG. 7 is a plan view of a lower substrate of a sample analyzing chip to which a bubble prevention channel is applied according to an embodiment of the present invention. FIG. 8 is a cross-sectional view of a sample analyzing chip to which a bubble prevention channel is applied according to an embodiment of the present invention. FIG. 9 is a cross-sectional view of a sample analyzing chip to which a bubble prevention channel of another form is applied according to an embodiment of the present invention.

Referring to FIGS. 5 to 9, a sample analyzing chip 1 according to an embodiment of the present invention may further include a bubble prevention channel 60 formed between the bonding area 103, 203 and a micro channel 22 and causing no wall surfaces to be formed around the micro channel 22 so as to suppress bubbles from being generated when a sample flows.

If the bubble prevention channel 60 is not formed, both sidewalls of the micro channel 22 are formed by the upper-substrate bonding area 103 and the lower-substrate bonding area 203 through which the upper substrate 10 and the lower substrate 200 are bonded to each other. Accordingly, when a sample is injected to flow through the sample analyzing chip 1, the sample first moves along the sidewalls and thus bubbles may occur in the micro channel 22, thereby interrupting the sample from being observed.

To solve this problem, an auxiliary channel such as the bubble prevention channel 60 is formed at both edges of the micro channel 22 to reduce the difference between flow rate of the sample due to the sidewalls, thereby stabilizing the flow of the sample.

In detail, the bubble prevention channel 60 is formed by a space defined by an upper-substrate groove 162 formed in the upper substrate 100 and a lower-substrate groove 262 formed in the lower substrate 200 as illustrated in FIG. 8.

The bubble prevention channel 60 is formed between the bonding area 103, 203 and the micro channel 22 along an edge of the body portion 20. Thus, the micro channel 22 may be formed such that no wall surfaces are formed at edges thereof.

Thus, a fluid may be suppressed from moving along wall surfaces of the micro channel 22 to prevent observing of the sample from being interfered by bubbles occurring in the micro channel 22.

The bubble prevention channel 60 may be formed only by the upper-substrate groove 162 as illustrated in FIG. 9. In this case, a portion of the micro channel 22 formed in the lower substrate 200 extends to both sides by a predetermined length to be wider than a portion of the micro channel 22 formed in the upper substrate 100. The extended portion of the micro channel 22 and the upper-substrate groove 162 form the bubble prevention channel 60 together.

The revere is possible. That is, the bubble prevention channel 60 may be formed only by the lower-substrate groove 262 without using the upper-substrate groove 162.

Figure 10:
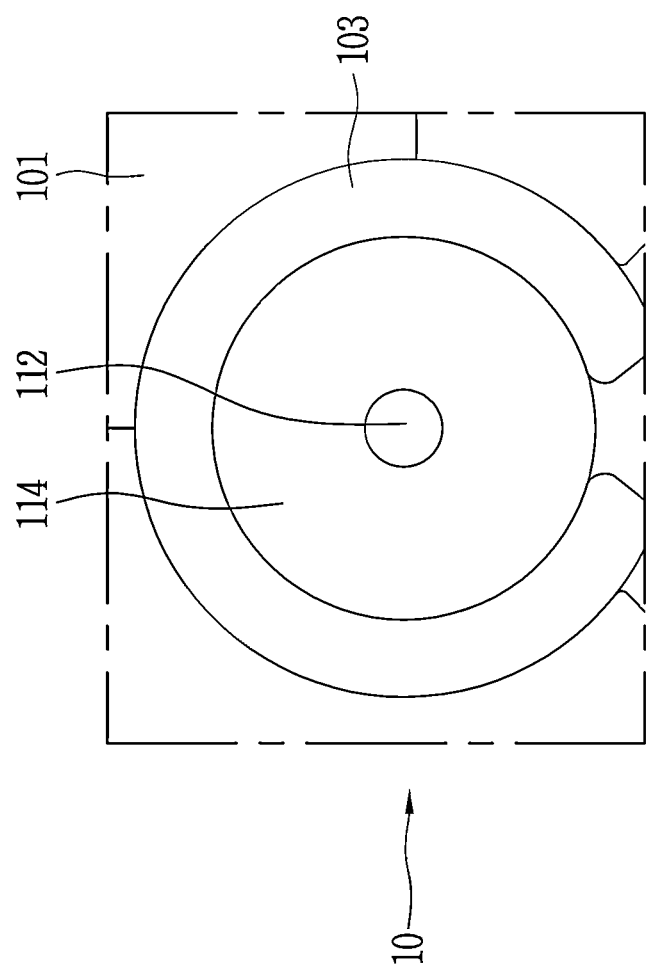
FIG. 10 is a partial plan view of an inlet of a sample analyzing chip according to an embodiment of the present invention.
Figure 11:
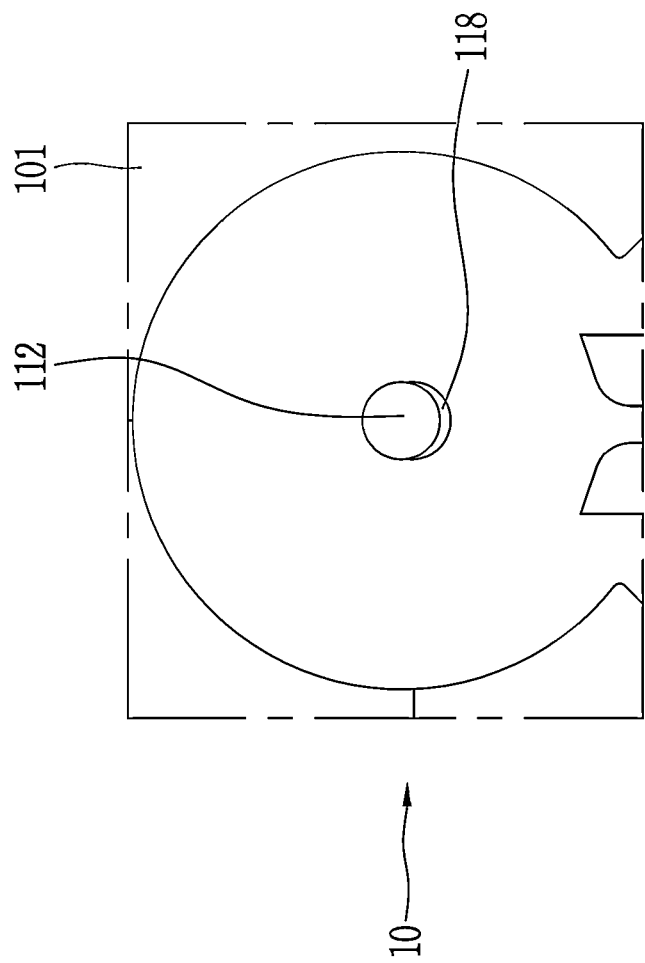
FIG. 11 is a partial bottom view of an inlet of a sample analyzing chip according to an embodiment of the present invention.
Figure 12:
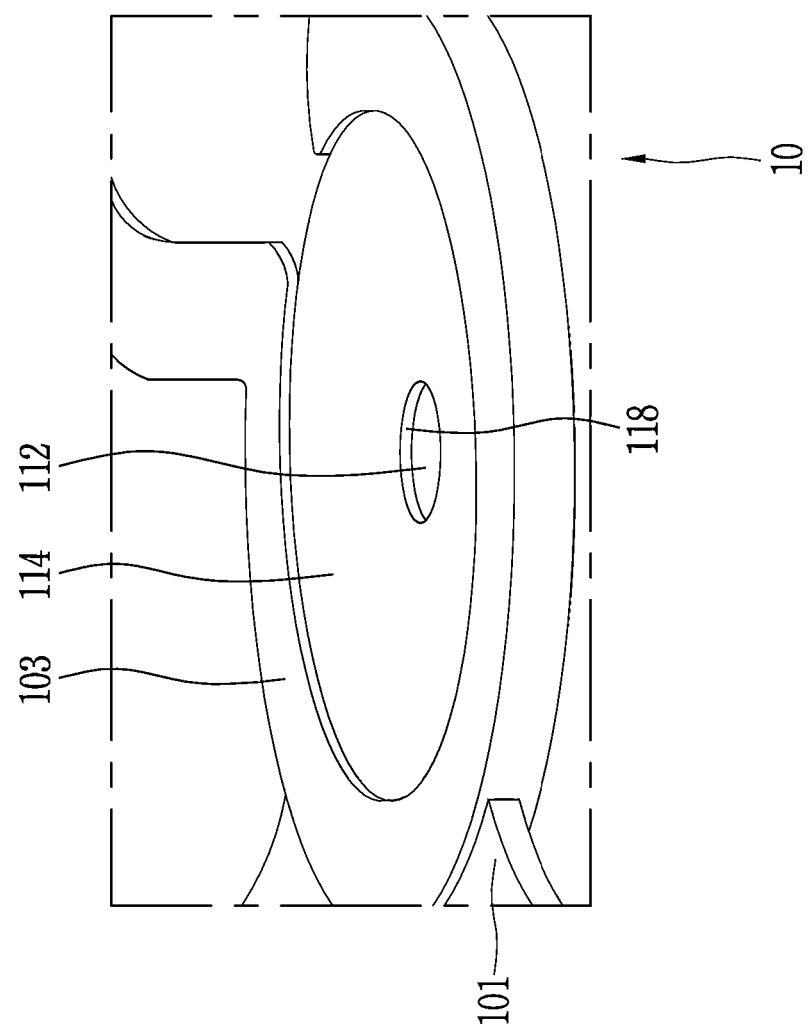
FIG. 12 is a partial perspective view of an inlet of a sample analyzing chip according to an embodiment of the present invention.
Figure 13:
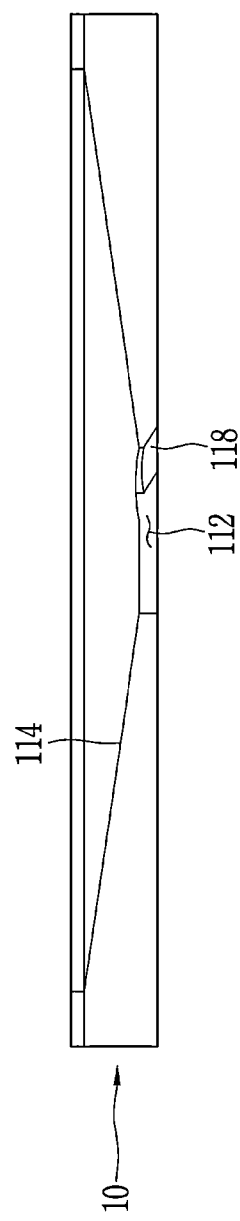
FIG. 13 is a partial cross-sectional view of an inlet of a sample analyzing chip according to an embodiment of the present invention.
Figure 14:
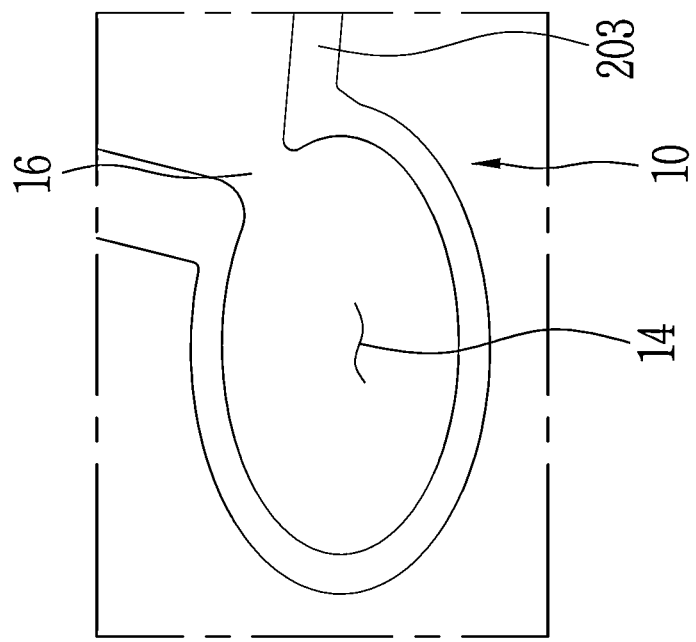
FIG. 14 is a partial perspective view of an inlet chamber formed at an inlet of a sample analyzing chip according to an embodiment of the present invention.

FIG. 10 is a partial plan view of an inlet of a sample analyzing chip according to an embodiment of the present invention. FIG. 11 is a partial bottom view of an inlet of a sample analyzing chip according to an embodiment of the present invention. FIG. 12 is a partial perspective view of an inlet of a sample analyzing chip according to an embodiment of the present invention. FIG. 13 is a partial cross-sectional view of an inlet of a sample analyzing chip according to an embodiment of the present invention. FIG. 14 is a partial perspective view of an inlet chamber formed at an inlet of a sample analyzing chip according to an embodiment of the present invention.

Referring to FIGS. 1 to 7 and 10 to 14, in the sample analyzing chip 1 according to an embodiment of the present invention, an inlet 10 through which a sample is injected is formed at a side of the micro channel 22. The inlet 10 communicates with the micro channel 22 to cause the injected sample to flow in the micro channel 22 by a capillary force.

Although the inlet 10 is formed in a round shape in the present embodiment, the inlet 10 is not limited to the round shape and may be formed in various other shapes if needed. The upper-substrate bonding area 103 is formed along an edge of the inlet 10 and bonded to the lower-substrate bonding area 203 corresponding to the lower substrate 200.

A drop hole 112 via which the sample flows into the inlet 10 may be formed in a center of the inlet 10. A curved surface portion 114 for uniformly supplying the sample may be formed to cause the sample dropped into the inlet 10 to remain in the drop hole 112 not to dry.

A groove is formed to be sunken to a predetermined depth in a portion of the inlet 10 formed in the lower substrate 200. Thus, an inlet chamber 14 forming a space is formed when the lower substrate 200 is combined with the upper substrate 100.

After the sample is injected, the sample cannot be measured or observed when the sample flows at a high speed. Thus, the inlet chamber 14 temporarily accommodates the sample injected via the drop hole 112, i.e., performs sample buffering, thereby rapidly stabilizing the flow of the sample.

An opening 118 that is cut to form a predetermined inclination toward the micro channel 22 may be formed at a side of the drop hole 112. The opening 118 prevents the sample flowing into the drop hole 112 from forming an interface and being gathered on a position due to surface tension without flowing into the inlet chamber 14.

Thus, when the sample injected into the inlet 10 passes through the drop hole 112, the sample does not form an interface in the form of drops and may smoothly flow into the inlet chamber 14 and finally flow toward the micro channel 22.

A first bottleneck 16 may be formed between the inlet 10 and the micro channel 22 to provide a narrower path than the micro channel 22. The first bottleneck 16 prevents the sample in the inlet chamber 14 from excessively flowing into the micro channel 22.

That is, similar to the inlet chamber 14, the first bottleneck 16 prevents the sample flowing at a high speed from the inlet chamber 14 into the micro channel 22, i.e., performs sample buffering. Thus, the flow and flow rate of the sample may be controlled to rapidly stabilize the flow of the sample.

Also, since the injected sample may be prevented from flowing toward the micro channel 22 and being discharged from the micro channel 22 at once, the sample does not dry within a short time, thereby guaranteeing stable measurement of the sample.

Figure 15:
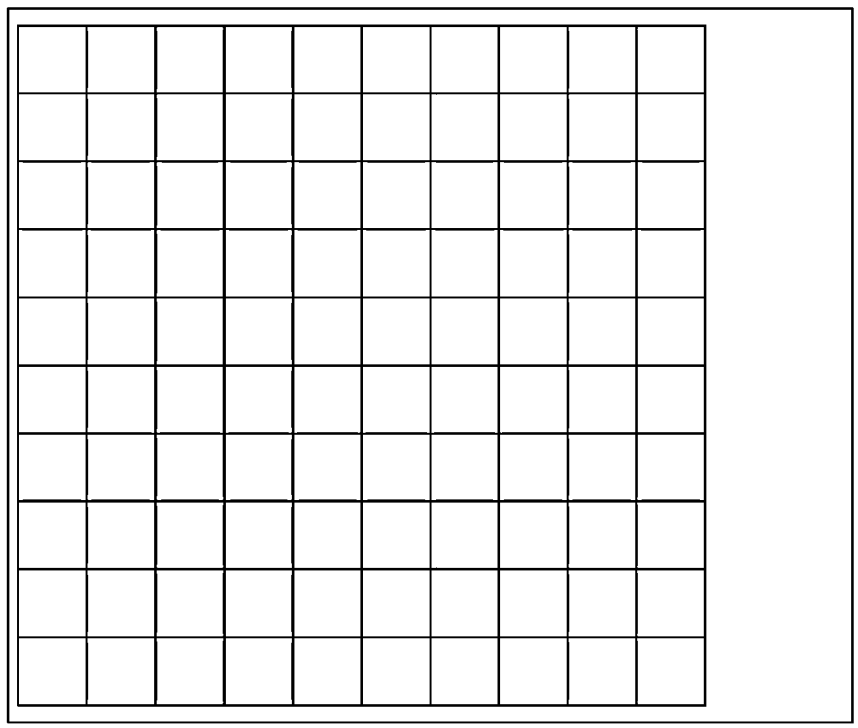
FIG. 15 is a partial plan view of a grid of a sample analyzing chip according to an embodiment of the present invention.
Figure 17:
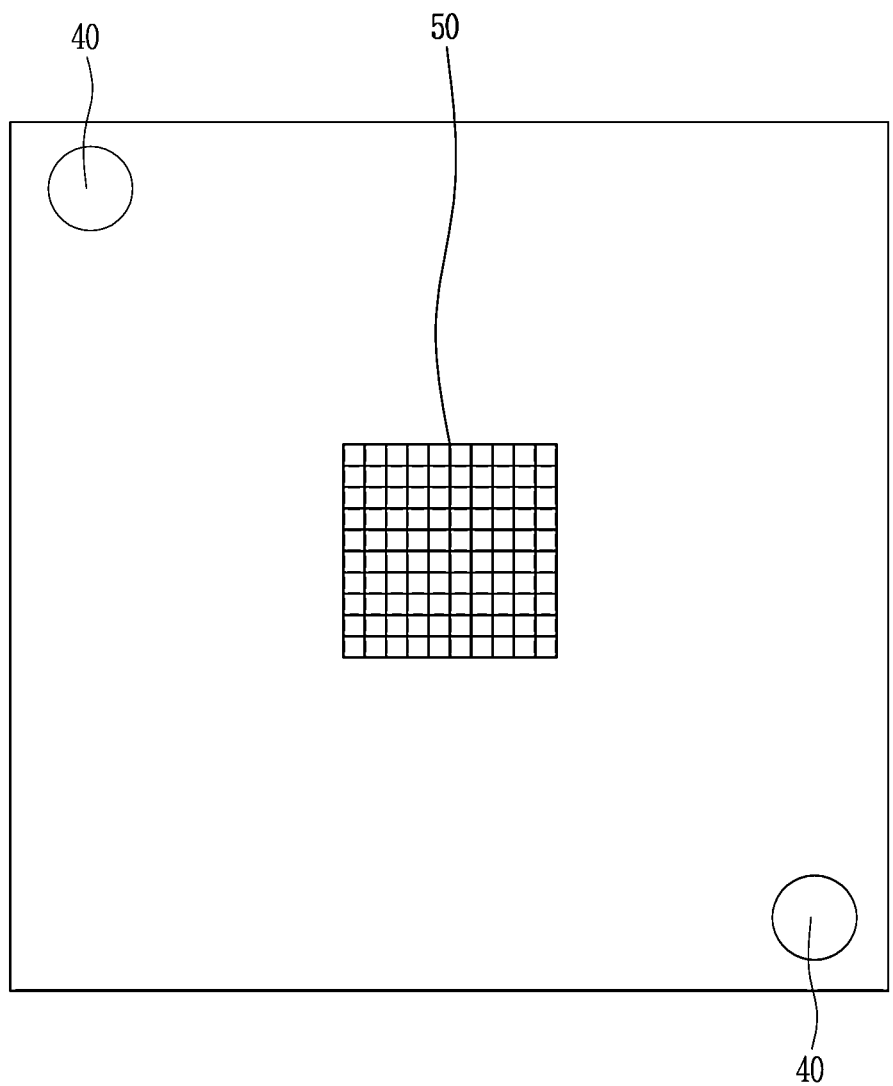
FIG. 17 is a partial plan view of a grid and micro pillars of a sample analyzing chip according to an embodiment of the present invention.
Figure 18:
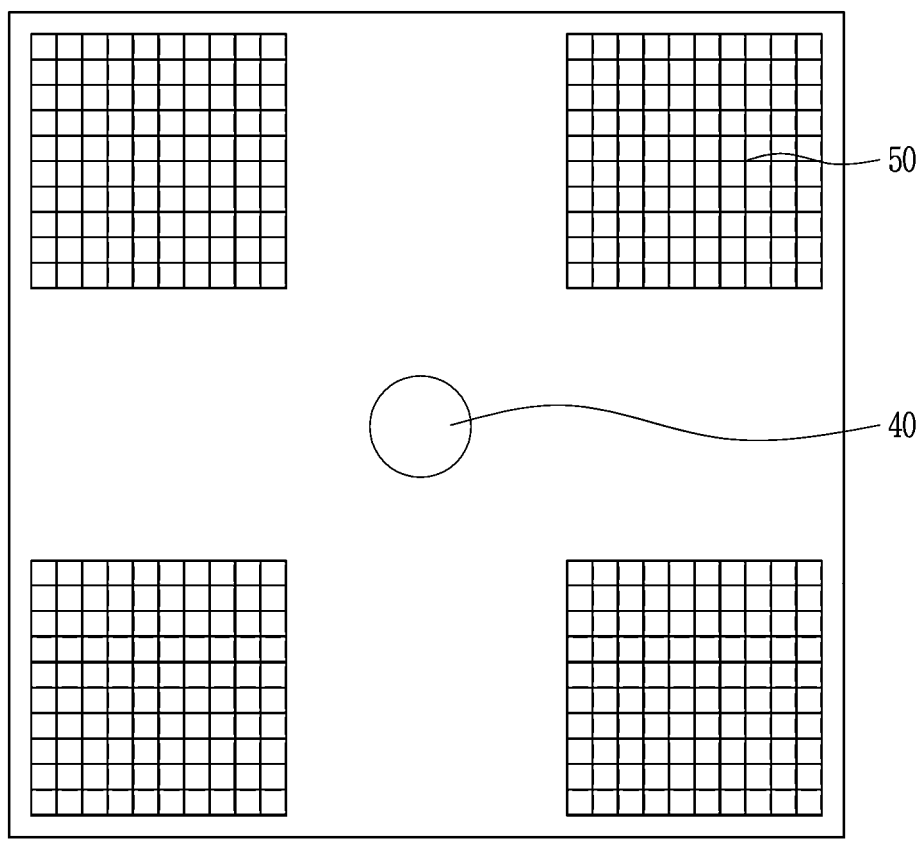
FIG. 18 is a partial plan view of a grid and micro pillars of another form of a sample analyzing chip according to an embodiment of the present invention.

FIG. 15 is a partial plan view of a grid of a sample analyzing chip according to an embodiment of the present invention. FIG. 16 is a partial cross-sectional view of an embossed or engraved grid of a sample analyzing chip according to an embodiment of the present invention. FIG. 17 is a partial plan view of a grid and micro pillars of a sample analyzing chip according to an embodiment of the present invention. FIG. 18 is a partial plan view of a grid and micro pillars of another form of a sample analyzing chip according to an embodiment of the present invention.

Referring to FIGS. 1 to 7 and 15 to 18, the sample analyzing chip 1 according to an embodiment of the present invention may include a grid 50 formed to observe a sample on the micro channel 22.

The grid 50 is a micro structure formed on the micro channel 22. The number of targets contained in a sample on the grid 50 is counted or the mobility of the targets is measured in a state in which the flow of the sample flowing into the micro channel 22 is stabilized.

As illustrated in FIG. 15, the grid 50 is formed in a lattice shape having a predetermined size. The whole size of the grid 50 may be about 50 μm to about 150 μm, and the distances between the lattices may be about 1 μm to about 4 μm.

In the grid 50, the lattices may have an embossed (positive) or engraved (negative) cross section as illustrated in FIG. 16. In this case, the height of the embossed (positive) cross section or the depth of the engraved (negative) cross section are formed to be about 1 μm to about 4 μm to be equal to the distances between the lattices.

Whether the grid 50 has an embossed (positive) shape or an engraved (negative) shape is determined by the type of the sample. For example, when the sample is bacteria, the bacteria are likely to be sunken into the grid 50 which has the engraved (negative) shape. Thus, the grid 50 should be formed in the embossed (positive) shape.

When the sample is sperm, the sperm are likely to be adhered to a protruding corner of the grid 50 which has the embossed (positive) shape. Thus, the grid 50 should be formed in the engraved (negative) shape.

In the present embodiment, one grid 50 is formed and two micro pillars 40 are disposed to be symmetrical to each other from the middle of one grid 50 as illustrated in FIG. 17, but the number of grids 50 may vary according to the type of a measured sample.

For example, four grids 50 may be formed and one micro pillar 40 may be disposed at the middle of the four grids 50 as illustrated in FIG. 18. Thus, the numbers and arrangement of the grids 50 and the micro pillars 40 may vary according to the type of a sample.

Figure 19:
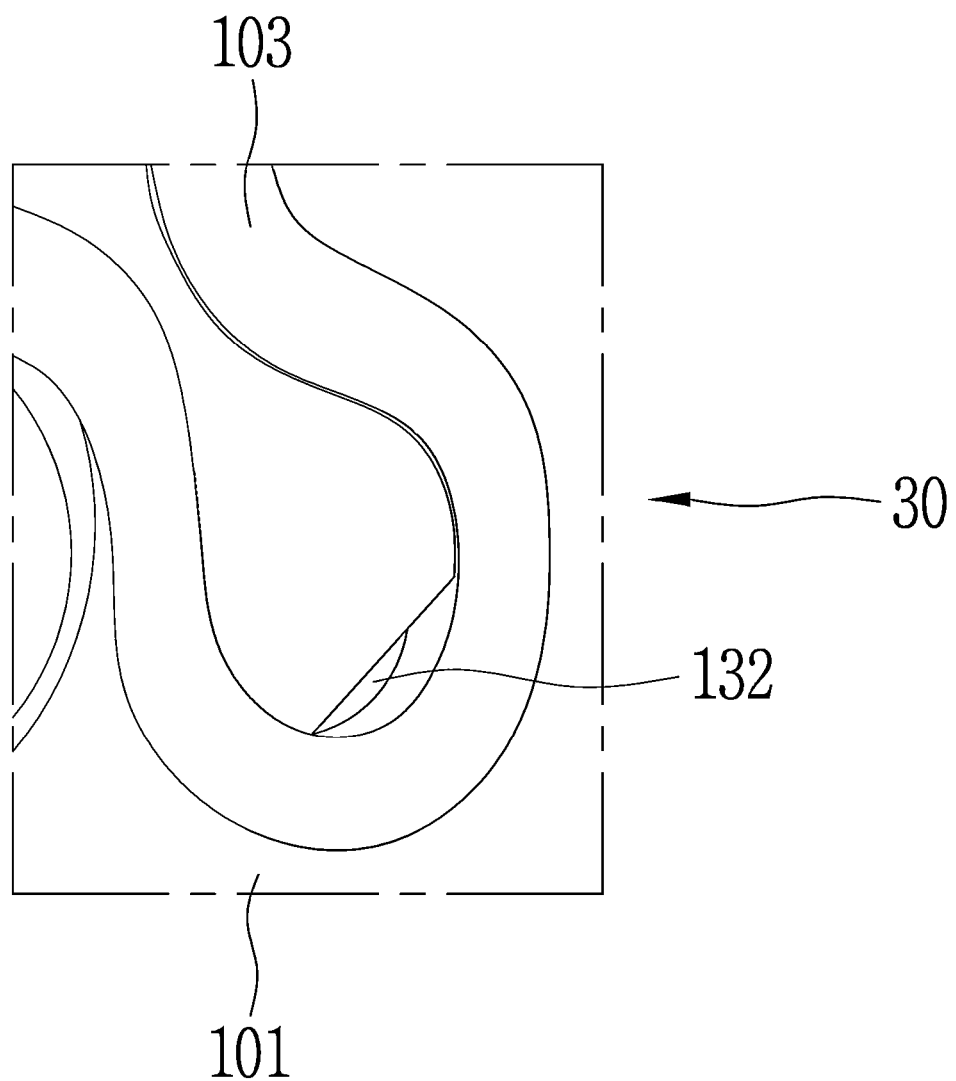
FIG. 19 is a partial perspective view of an outlet of a sample analyzing chip according to an embodiment of the present invention.
Figure 20:
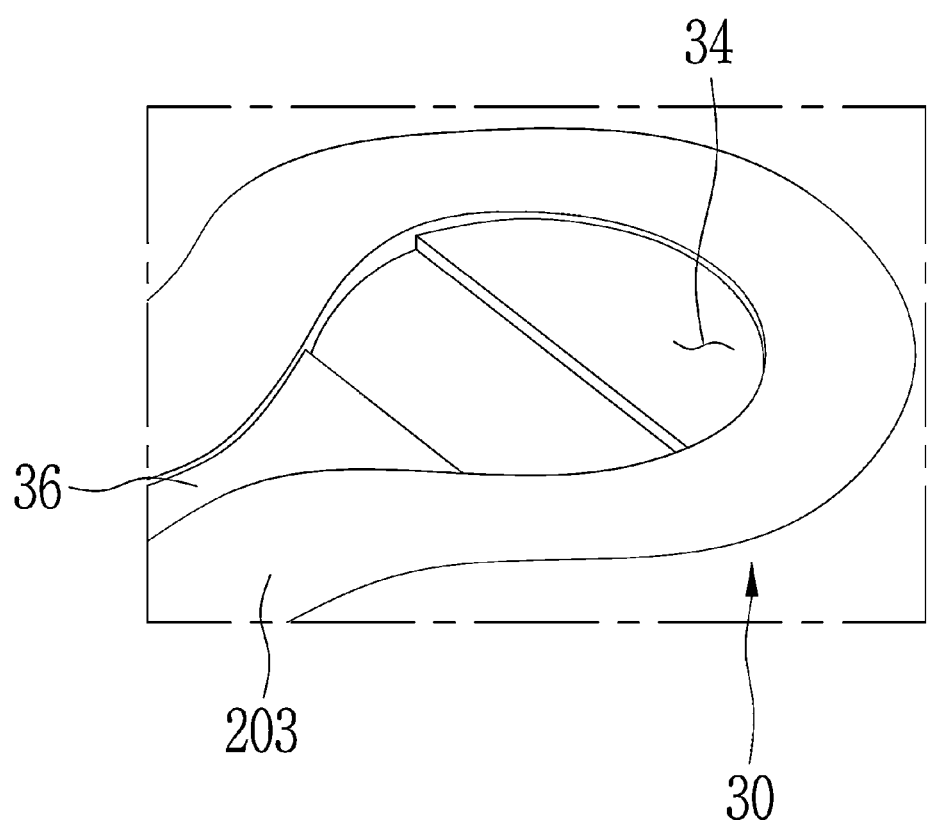
FIG. 20 is a partial perspective view of an outlet chamber formed at an outlet of a sample analyzing chip according to an embodiment of the present invention.

FIG. 19 is a partial perspective view of an outlet of a sample analyzing chip according to an embodiment of the present invention. FIG. 20 is a partial perspective view of an outlet chamber formed at an outlet of a sample analyzing chip according to an embodiment of the present invention.

Referring to FIGS. 1 to 7, 19, and 20, the sample analyzing chip 1 according to an embodiment of the present invention may further include an outlet 30 which is formed at another side of the micro channel 22 and through which a sample flows out from the micro channel 22. The outlet 30 communicates with the micro channel 22 to cause the sample flowing in the micro channel 22 to be discharged into the outlet 30.

Although the outlet 30 is formed in a round shape in the present invention, the outlet 30 is not limited to the round shape and may be formed in various other shapes if needed. The upper-substrate bonding area 103 is formed at an edge of the outlet 30 and bonded to the lower-substrate bonding area 203 corresponding to the lower substrate 200.

An open hole 132 may be formed at a side of the outlet 30 opposite to the micro channel 22. The open hole 132 causes the other side of the micro channel 22 to be an open end so that a sample may flow on the micro channel 22.

A groove is formed to be sunken to a predetermined depth in a portion of the outlet 30 of the lower substrate 200. Thus, when the lower substrate 200 is combined with the upper substrate 100, an outlet chamber 34 forming a predetermined space is formed. The outlet chamber 34 forms the predetermined space between the upper substrate 100 and the lower substrate 200 to accommodate the sample flowing out from the micro channel 22.

A second bottleneck 36 may be formed between the outlet 30 and the micro channel 22 to provide a narrower path than the micro channel 22. The second bottleneck 36 prevents the sample in the micro channel 22 from being rapidly discharged to the outlet chamber 34. Thus, the sample is prevented from drying rapidly, thereby guaranteeing stable measurement of the sample.

Figure 21:
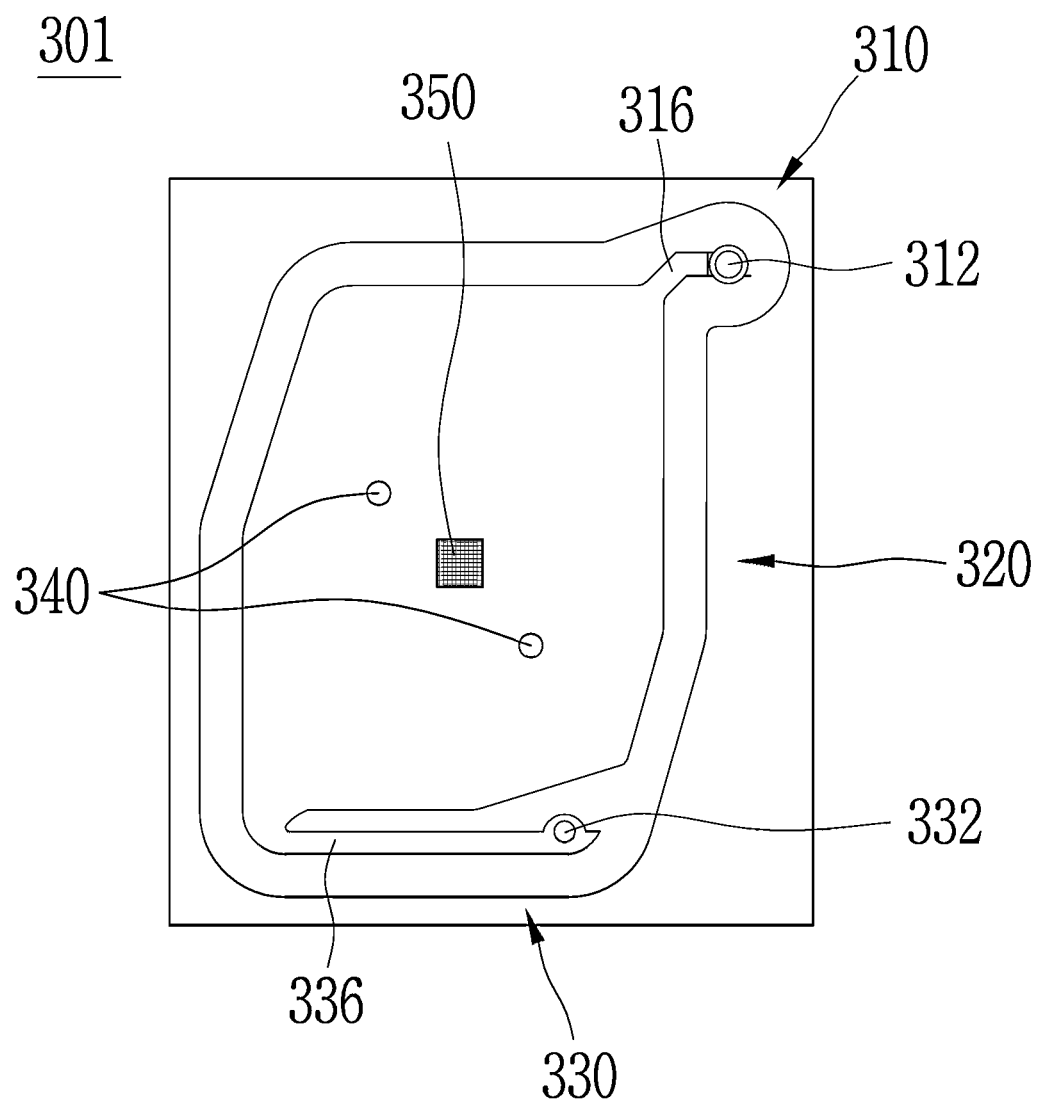
FIG. 21 is a plan view of a sample analyzing chip according to another embodiment of the present invention.
Figure 22:
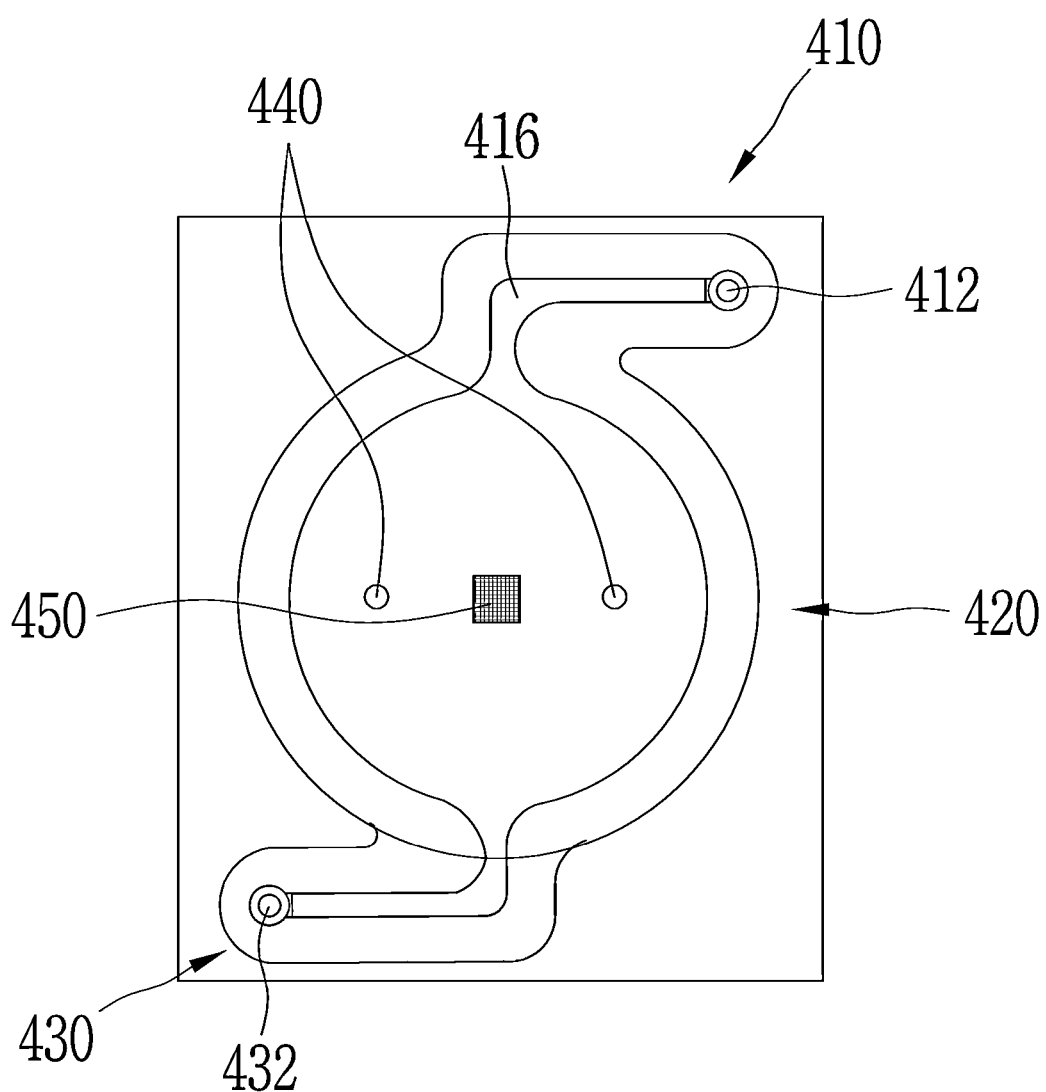
FIG. 22 is a plan view of a sample analyzing chip according to another embodiment of the present invention.

FIG. 21 is a plan view of a sample analyzing chip according to another embodiment of the present invention. FIG. 22 is a plan view of a sample analyzing chip according to another embodiment of the present invention.

FIGS. 21 and 22 illustrate sample analyzing chips 301 and 401 which are modified examples of the sample analyzing chip 1 according to the previous embodiment. Both the sample analyzing chips 301 and 401 are different from the sample analyzing chip 1 described above in terms of detailed design but are the same as the sample analyzing chip 1 in that they also include inlets 310 and 410, body portions 320 and 420, and outlets 330 and 430.

Drop holes 312 and 412 are formed in the inlets 310 and 410 such that a sample is injected via the drop holes 312 and 412. Micro pillars 340 and 440 and grids 350 and 450 are formed on the body portions 320 and 420 to maintain a height of a channel. Also, open holes 332 and 432 are formed at the outlets 330 and 430.

First bottlenecks 316 and 416 are formed between the inlets 310 and 410 and the body portions 320 and 420 and second bottlenecks 336 and 436 are formed between the outlets 330 and 430 and the body portions 320 and 420 to prevent the sample from rapidly flowing and evaporating, thereby enabling the sample to be stably measured.

As described above, the sample analyzing chip 1 according to an embodiment of the present invention may be embodied in various modified forms without departing from the technical features described above. The various modified examples should be understood to be within the technical idea of the present invention.

Figure 23:
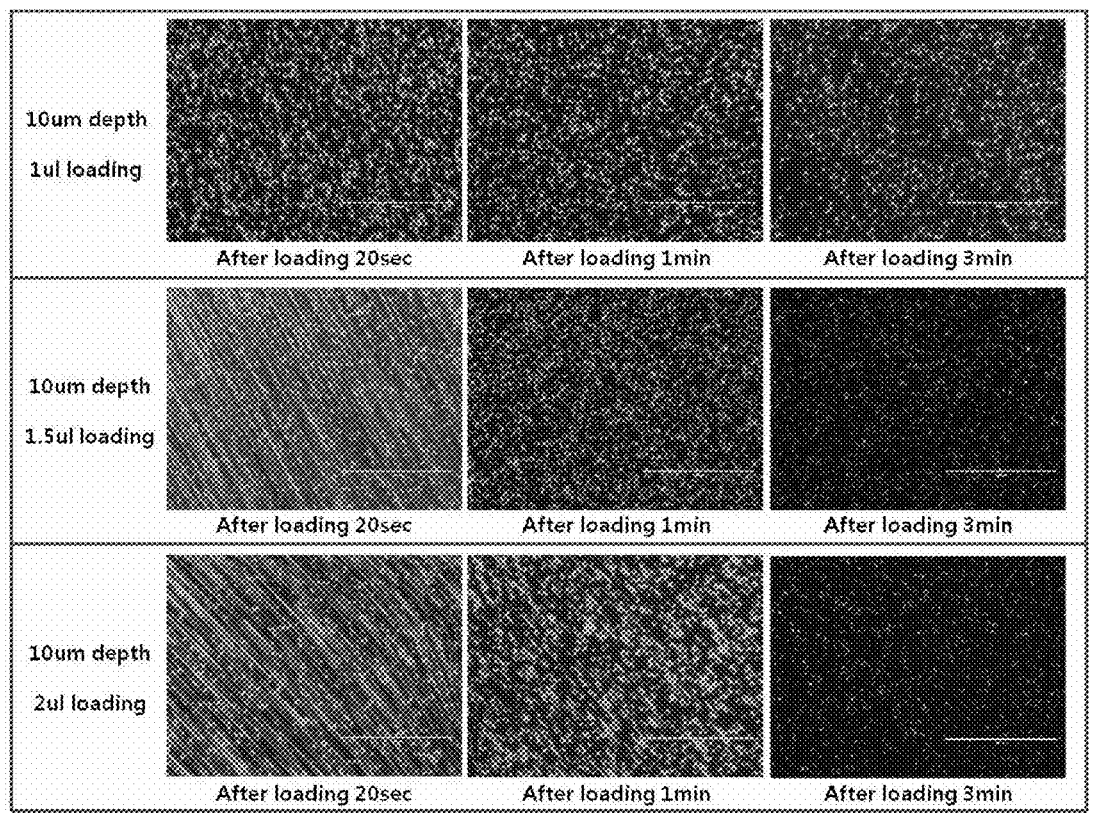
FIG. 23 is a photo showing a result of measuring a sample according to the amount of the sample injected and a time when a sample analyzing chip according to an embodiment of the present invention has a height of 10 μm.
Figure 24:
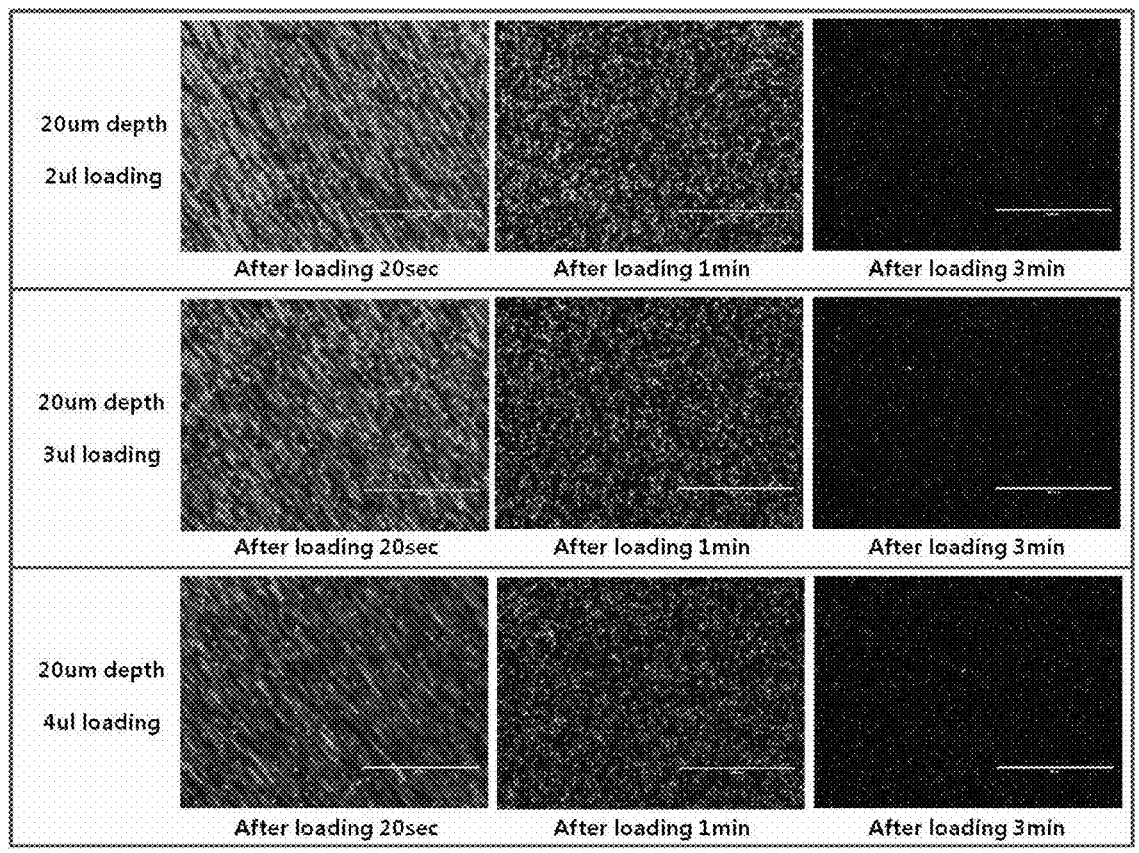
FIG. 24 is a photo showing a result of measuring a sample according to the amount of the sample injected and a time when a sample analyzing chip according to an embodiment of the present invention has a height of 20 μm.

FIGS. 23 and 24 are photos showing results of measuring a sample when a height of a sample analyzing chip according to an embodiment of the present invention is 10 μm and 20 μm. Referring to FIGS. 23 and 24, a flow of the sample was stabilized within a short time, and arrived at a state in which the number or mobility of a target can be measured about three minutes after the sample was injected.

Also, the sample analyzing chip 1 according to an embodiment of the present invention is capable of suppressing a sample from evaporating and drying as long as possible. Thus, the above state may be maintained for about twenty minutes so that an observer may measure a sample such as sperm, bacteria, platelets, etc.

In the sample analyzing chip 1 according to an embodiment of the present invention described above, the upper and lower substrates of the channel may be prevented from being adhered to each other due to deflection on a micro channel. Also, the present invention may solve the problem of the sample drying up within a measuring time of a target. Furthermore, bubbles are prevented from being generated due to different flow rate of the sample caused by a wall surface of the micro channel.

In addition, a time required to stabilize the flow of the sample may be minimized to reduce a duration for which micro cells can be measured.

Although the present invention has been described above with reference to the exemplary embodiments thereof, it would be understood by those skilled in the art that various changes and modifications may be made without departing from the technical idea and scope of the present invention. Thus, it is clear that all modifications are within the technical scope of the present invention as long as they include the components as recited in the claims of the present invention.

What is claimed is:

1. A sample analyzing chip comprising:
   a micro channel formed between an upper substrate and a lower substrate bonded to each other, and including a micro pillar and a bubble prevention channel;
   an inlet formed at one side of the micro channel, and including a first bottleneck configured to control a flow and a flow rate of an injected sample and delay drying of the sample; and
   an outlet formed at another side of the micro channel, and including a second bottleneck configured to delay flowing of the sample out from the micro channel and drying of the sample.

2. The sample analyzing chip of claim 1, wherein the micro pillar is formed on at least one of the upper substrate and lower substrate and is configured to maintain a height of the micro channel.

3. The sample analyzing chip of claim 1, wherein the bubble prevention channel is formed by a step formed in a peripheral region near the micro channel, and configured to suppress bubbles by minimizing the difference between flow rate of the sample when the sample flows.

4. The sample analyzing chip of claim 1, further comprising a grid formed to observe the sample on the micro channel.

5. The sample analyzing chip of claim 1, wherein the inlet comprises:
   a drop hole formed in the upper substrate and through which the sample is injected into the sample analyzing chip; and
   a curved surface portion forming an inclined curved surface toward the drop hole.

6. The sample analyzing chip of claim 5, wherein the inlet further comprises an inlet chamber forming a space between the upper substrate and the lower substrate, and configured to accommodate the sample injected via the drop hole.

7. The sample analyzing chip of claim 5, wherein the inlet further comprises an opening formed at a side of the drop hole and configured to cause the injected sample to smoothly flow toward the micro channel without forming an interface.

8. The sample analyzing chip of claim 4, wherein the grid is formed in an embossed or engraved shape according to the type of the injected sample.

9. The sample analyzing chip of claim 1, wherein the upper substrate and the lower substrate are combined by bonding a bonding area to each other, wherein the bonding area protrudes from edges of a bottom surface of the upper substrate and a top surface of the lower substrate around the micro channel.

10. The sample analyzing chip of claim 1, wherein the outlet comprises:
    an open hole formed at a side of the outlet opposite to the micro channel; and
    an outlet chamber forming a space between the upper substrate and the lower substrate, and configured to accommodate the sample flowing out from the micro channel so as to stabilize the overall flow of the sample.

11. A sample analyzing chip comprising:
    a micro channel;
    at least one micro pillar configured to maintain a height of the micro channel;
    a grid formed to observe a sample on the micro channel; and
    a bubble prevention channel configured to suppress bubbles from being generated when the sample flows near the micro channel.

12. A sample analyzing chip comprising:
    an inlet into which a sample is injected;
    a micro channel communicating with the inlet to cause the injected sample to flow,
    wherein the micro channel comprises:
    a micro pillar configured to maintain a height of a section in which the sample flows; and
    a grid formed to observe the sample;
    an outlet through which the sample flows out from the micro channel; and
    a bottleneck formed between the inlet and the micro channel and between the outlet and the micro channel and configured to provide a narrower path than the micro channel.

* * * * *